US011213340B2

(12) United States Patent
Su et al.

(10) Patent No.: US 11,213,340 B2
(45) Date of Patent: Jan. 4, 2022

(54) THERAPY TO TREAT PELVIC FLOOR DYSFUNCTION AND/OR PAIN

(71) Applicant: Medtronic, Inc., Minneapolis, MN (US)

(72) Inventors: Xin Su, Plymouth, MN (US); Dwight E. Nelson, Shoreview, MN (US); Jason E. Agran, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 654 days.

(21) Appl. No.: 15/130,344

(22) Filed: Apr. 15, 2016

(65) Prior Publication Data
US 2017/0105784 A1  Apr. 20, 2017

Related U.S. Application Data

(60) Provisional application No. 62/242,922, filed on Oct. 16, 2015.

(51) Int. Cl.
*A61B 18/12* (2006.01)
*A61B 18/00* (2006.01)
*A61B 18/14* (2006.01)

(52) U.S. Cl.
CPC ...... *A61B 18/1233* (2013.01); *A61B 18/1492* (2013.01); *A61B 2018/00434* (2013.01); *A61B 2018/00517* (2013.01); *A61B 2018/00577* (2013.01); *A61B 2018/00791* (2013.01)

(58) Field of Classification Search
CPC ........... A61B 2018/00517; A61B 2018/00434; A61B 2018/00577; A61B 2018/00791; A61B 18/1233; A61B 18/142
See application file for complete search history.

(56) References Cited

U.S. PATENT DOCUMENTS

| 6,692,490 | B1 | 2/2004 | Edwards |
| 2012/0089123 | A1* | 4/2012 | Organ ............... A61B 18/1492 604/523 |
| 2012/0128762 | A1 | 5/2012 | Chancellor et al. |
| 2013/0085489 | A1* | 4/2013 | Fain .................. A61N 1/36007 606/34 |
| 2014/0039356 | A1* | 2/2014 | Sachs .................... A61B 18/24 606/27 |

(Continued)

OTHER PUBLICATIONS

Kenton et al., "Urethral and bladder current perception thresholds: Normative data in women," J. Urol 2007; vol. 178, No. 1, Jul. 2007; pp. 189-192.

(Continued)

*Primary Examiner* — Joseph A Stoklosa
*Assistant Examiner* — Rachel A. Vierra
(74) *Attorney, Agent, or Firm* — Patterson Thuente Pedersen, P.A.

(57) ABSTRACT

In some examples, the disclosure describes devices, systems, and techniques for treating pain and/or pelvic floor dysfunction of a patient. For example, a method for treating pelvic floor dysfunction in a patient may include delivering, via a medical device, a therapy to one or more nerve fibers, wherein the therapy is configured to at least temporarily deactivate the one or more nerve fibers; and determining that the one or more nerve fibers was at least temporarily deactivated by delivering the therapy.

9 Claims, 12 Drawing Sheets

(56) References Cited

U.S. PATENT DOCUMENTS

| | | | | |
|---|---|---|---|---|
| 2014/0073903 | A1* | 3/2014 | Weber | A61B 18/1206 |
| | | | | 606/34 |
| 2014/0142549 | A1* | 5/2014 | Su | A61N 1/36171 |
| | | | | 604/512 |
| 2014/0257268 | A1 | 9/2014 | Sachs et al. | |
| 2014/0276718 | A1* | 9/2014 | Turovskiy | A61B 18/082 |
| | | | | 606/31 |
| 2014/0330267 | A1* | 11/2014 | Harrington | A61B 18/1206 |
| | | | | 606/34 |
| 2016/0045747 | A1* | 2/2016 | Jiang | A61N 1/37241 |
| | | | | 607/40 |
| 2016/0128767 | A1* | 5/2016 | Azamian | A61B 18/1492 |
| | | | | 606/41 |

OTHER PUBLICATIONS

Habler et al., "Activation of unmyelinated afferent fibres by mechanical stimuli and inflammation of the urinary bladder n the cat," Physiology 1990; 425, pp. 545-562 (Applicant points out, in accordance with MPEP 609.04(a), that the year of publication, 1990, is sufficiently earlier than the effective U.S. filing date so that the particular month of publication is not in issue.).

de Groat WC, et al., "Mechanisms underlying the recovery of urinary bladder function following spinal cord injury," J Auton Nerv Syst 1995; pp. 493-505 (Applicant points out, in accordance with MPEP 609.04(a), that the year of publication, 1995, is sufficiently earlier than the effective U.S. filing date so that the particular month of publication is not in issue.).

Vijaya et al., "Antimuscarinic effects on current perception threshold: a prospective placebo control study," Neurourol Urodyn. Jan. 2012; 31(1):75-9, 6 pp.

Andersson et al., "Rodent models for urodynamic investigation" Neurourol Urodyn, Jun. 2011, 30:636-646, 11 pp.

Andersson et al., "Muscarinic acetylcholine receptors in the urinary tract," Handbook Exp Pharmacol 202:319-44, 2011. (Applicant points out, in accordance with MPEP 609.04(a), that the year of publication, 2011, is sufficiently earlier than the effective U.S. filing date so that the particular month of publication is not in issue.).

de Groat WC, et al., Reorganization of sympathetic preganglionic connections in cat bladder ganglia following parasympathetic denervation. 1989, J Physiol. 409: pp. 431-449 (Applicant points out, in accordance with MPEP 609.04(a), that the year of publication, 1989, is sufficiently earlier than the effective U.S. filing date so that the particular month of publication is not in issue.).

Gribovskaja-Rupp, et al., "Upregulation of mucosal 5-HT3 receptors is involved in restoration of colonic transit after pelvic nerve transection." Neurogastroenterol Motil. 24:472-8, May 2012, 9 pp.

Häbler HJ, et al., "Receptive properties of myelinated primary afferents innervating the inflamed urinary bladder of the cat." J Neurophysiol Feb. 1993, 69: pp. 395-405.

Hirotsu, et al. "Effect of muscarinic agonist on overflow incontinence induced by bilateral pelvic nerve transection in rats." Jpn J Pharmacol. 76(1): pp. 109-111, Jan. 1998.

Keast JR, et al,. "Distribution of neurons in the major pelvic ganglion of the rat which supply the bladder, colon or penis," Cell Tissue Res. Apr. 1989; 256(1):105-12.

Kwon, et al., "Neurologic recovery and improved detrusor contractility using muscle-derived cells in rat model of unilateral pelvic nerve transection." Urology 65:1249-53, Jun. 2005, 5 pp.

Long et al. "Clinical efficacy and safety of nerve-sparing radical hysterectomy for cervical cancer: a systematic review and meta-analysis." PLoS One. 9:e94116, Apr. 2014, 14 pp.

Meerts et al. "Conditioned place preference for mating is preserved in rats with pelvic nerve transection." Behav Neurosci. 123: 539-46, Nov. 2009, 15 pp.

Moss et al,. "Pressure, volume, and chemosensitivity in afferent innervation of urinary bladder in rats." Am J Physiol Regul Integr Comp Physiol vol. 272, No. 2; R695-R703, Feb. 1997.

Sengupta et al., "Mechanosensitive properties of pelvic nerve afferent fibers innervating the urinary bladder of the rat." J Neurophysiol, Nov. 1994, 72: 2420-2430.

Su, et al., "Effects of opioids on mechanosensitive pelvic nerve afferent fibers innervating the urinary bladder of the rat." J Neurophysiol; Mar. 1997, 77: pp. 1566-1580.

Su, et al., "Neuromodulation attenuates bladder hyperactivity in a rat cystitis model." BMC UroL Dec. 2013; 13:70. doi: 10.1186/1471-2490-13-70, 7 pp.

Uemura et al., "Distribution of lumbar and sacral afferent axons in submucosa of cat urinary bladder." Anat Rec 183:579-587, Dec. 1975.

Fall et al. "A bladder-to-bladder cooling reflex in the cat." J Physiol Aug. 1990; 427: pp. 281-300.

Andersson, "Bladder activation: Afferent mechanism." Urology May 2002; 59:43-50.

* cited by examiner

Table 1. Cystometry parameters in rats received no pelvic nerve manipulations (naive) or partial bladder denervation following intravesical infusion of saline or acetic acid

| | BP (mmHg) | MP (mmHg) | TP (mmHg) | VD (sec) | ICI (min) |
|---|---|---|---|---|---|
| saline (30 min) | | | | | |
| naive | 17.52 ± 0.98 | 44.04 ± 1.78 | 23.64 ± 1.58 | 44.21 ± 6.56 | 13.01 ± 1.64 |
| PBD | 21.61 ± 1.75 | 47.47 ± 1.57 | 28.90 ± 1.51 | 55.65 ± 5.08 | 11.54 ± 1.32 |
| a.a. (30 min) | | | | | |
| naive | 26.03 ± 1.82* | 47.59 ± 1.68 | 28.96 ± 2.07 | 29.94 ± 2.99 | 3.20 ± 0.59*# |
| PBD | 22.43 ± 1.28 | 45.83 ± 1.46 | 27.20 ± 1.58 | 42.64 ± 4.04 | 7.25 ± 0.79*#~ |

PBD: partial bladder denervation, a.a.: acetic acid, BP: basal pressure, MP: maximum pressure, TP: threshold pressure, VD: void duration, ICI: intercontraction interval.

$P<0.05$, ANOVA, Tukey's post test for intergroup comparison to saline naïve rats (*), to saline partial rats (#), and to a.a. naïve rats (~).

FIG. 10

THERAPY TO TREAT PELVIC FLOOR DYSFUNCTION AND/OR PAIN

This application claims the benefit of U.S. provisional patent application No. 62/242,922 by Su et al. and filed Oct. 16, 2015. The entire contents of this provisional application are incorporated by reference herein.

TECHNICAL FIELD

In some examples, the disclosure relates to medical therapies and, more particularly, therapy for treating bladder dysfunction or other pelvic floor dysfunction(s).

BACKGROUND

Bladder dysfunction, such as, e.g., overactive bladder, urgency, or urinary incontinence, and bladder pain or pelvic pain, are problems that may afflict people of all ages, genders, and races. Various muscles, nerves, organs and conduits within the pelvic floor cooperate to collect, store and release urine. A variety of disorders may compromise urinary function, and contribute to an overactive bladder, urgency, and/or urinary incontinence. Many of the disorders may be associated with aging, injury or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence.

In some cases, urinary incontinence can be attributed to improper sphincter function, either in the internal urinary sphincter or external urinary sphincter. For example, aging can result in weakened sphincter muscles, which may cause incontinence. Nerves running though the pelvic floor stimulate contractility in the sphincter. An improper communication between the nervous system and the urethra or urinary sphincter can result in a bladder dysfunction, such as overactive bladder, urgency, urge incontinence, or another type of urinary incontinence.

SUMMARY

In some aspects, the disclosure is directed to techniques and/or systems for identifying and/or treating pelvic floor dysfunctions, such as, e.g., pelvic pain or bladder dysfunction such as urinary incontinence. The pelvic floor disorder may be caused, at least in part, by activations of nerve fibers, such as, e.g., group C nerve fibers (also referred to herein a "C fibers" and "C nerve fibers") or other unmyelinated nerve fibers. In some examples, to treat the pelvic floor dysfunction, a clinician may identify one or more C fibers exhibiting undesirable nerve activity, e.g., C fiber nerve activity that is associated with pathological manifestations or symptoms of the pelvic dysfunction. Any of a variety of suitable techniques may be employed to identify such C fibers activity in a patient. A clinician may target at least a portion of C fibers (e.g., C fibers previously identified by a clinician) for the delivery of therapy via a medical device, where the therapy is configured to temporarily or permanently deactivate the C fibers. Examples of such therapy may include, but are not limited to, ablation therapy or mechanical stretching of the C fibers within the patient. In some examples, following delivery of the therapy, one or more techniques may be employed to confirm that the therapy has successfully deactivated C fibers. If it is determined that the therapy was not successful, the therapy may be redelivered, e.g., the therapy may be redelivered after making one or more modifications to the original therapy, to deactivate C fibers.

In one example, the disclosure relates to a method comprising delivering, via a medical device, a therapy to one or more nerve fibers of a patient, wherein the therapy is configured to at least temporarily deactivate the one or more nerve fibers to treat pain and/or pelvic floor dysfunction of the patient; and determining whether the one or more nerve fibers was at least temporarily deactivated by delivering the therapy.

In another example, the disclosure is directed to a method for treating to treat pain and/or pelvic floor dysfunction in a patient, the method comprising identifying one or more group C nerve fibers of patient to target for delivery of therapy via a medical device to treat the pelvic floor dysfunction; controlling the delivery of therapy via the medical device to the one or more group C nerve fibers, wherein the therapy is configured to at least temporarily deactivate the one or more identified group C nerve fibers; and determining the one or more group C fibers was at least temporarily deactivated by the delivered therapy.

In another example, the disclosure is related to a medical device system comprising a therapy module configured to deliver therapy to treat pain and/or pelvic floor dysfunction in a patient; and a processor configured to control the therapy module to deliver the therapy to one or more nerve fibers of the patient, wherein the therapy is configured to at least temporarily deactivate the one or more nerve fibers; and determine whether the one or more nerve fibers was at least temporarily deactivated by delivery of the therapy.

In another example, the disclosure is related to a medical device system comprising means for delivering, via a medical device, a therapy to one or more nerve fibers, wherein the therapy is configured to at least temporarily deactivate the one or more nerve fibers to treat pain and/or pelvic floor dysfunction of the patient; and means for determining whether the one or more nerve fibers was at least temporarily deactivated by delivering the therapy.

The details of one or more examples are set forth in the accompanying drawings and the description below. Other features, objects, and advantages will be apparent from the description and drawings, and from the claims.

BRIEF DESCRIPTION OF DRAWINGS

FIGS. 5A-5G, 6A-6B, 7A-7B, 8A-8B, 9A-9E, and 10 are various plots and diagrams relating to an experimental study carried out to evaluate one or more aspects of the disclosure.

DETAILED DESCRIPTION

Figure 1:
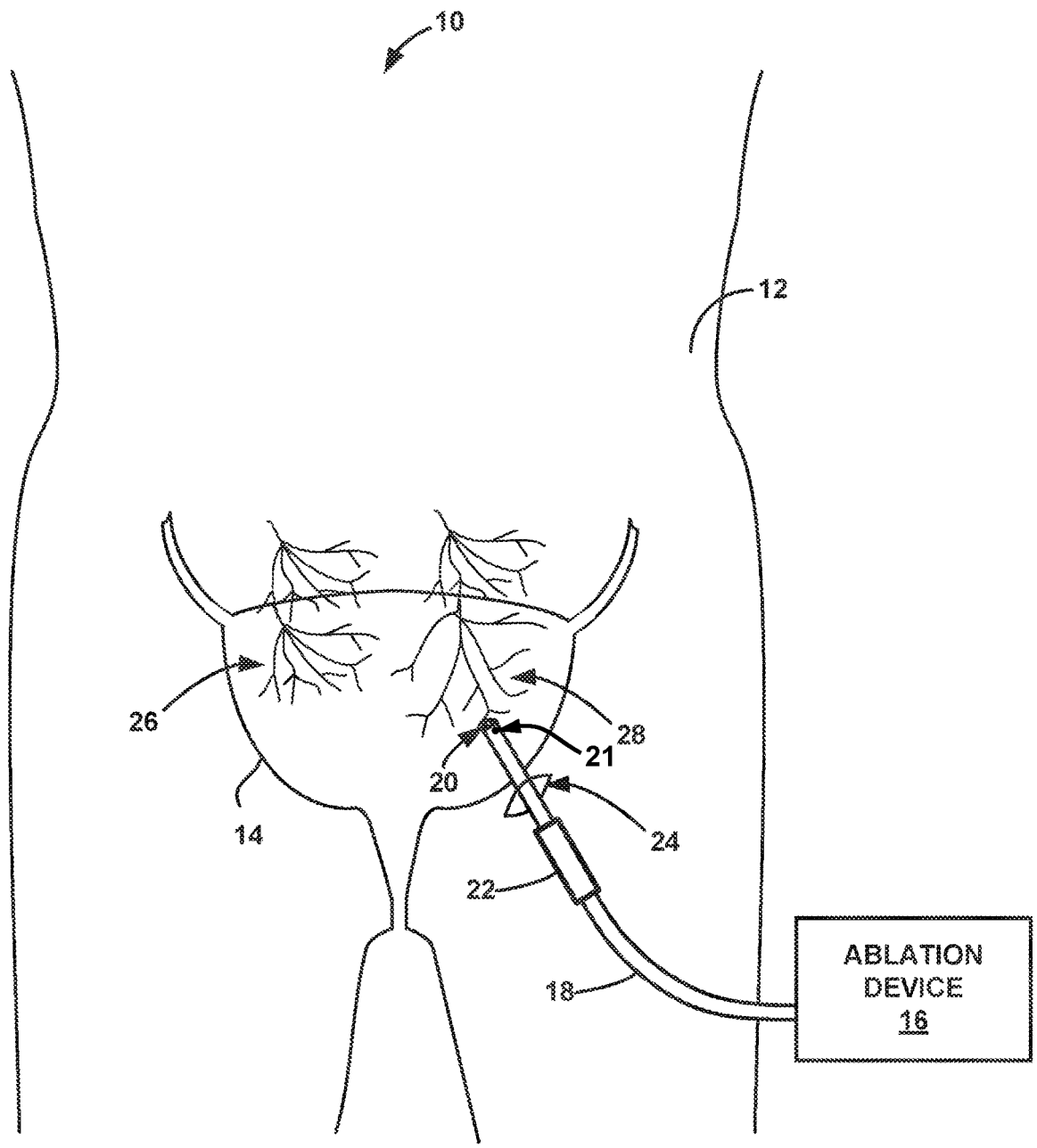
FIG. 1 is a conceptual diagram illustrating an example system that ablates targeted portions of nerve or muscle tissue external of the bladder, according to one or more aspects disclosed herein.

In some examples, the disclosure is directed to techniques and systems for treating pelvic floor dysfunction of a patient, such as, e.g., pelvic pain or bladder dysfunction. Bladder dysfunction generally refers to a condition of improper functioning of the bladder or urinary tract, and may include, for example, an overactive bladder, urgency, and urinary incontinence. Urgency is a sudden, compelling urge to urinate, and may often, though not always, be associated with urinary incontinence. Overactive bladder may include excessive contractions of the detrusor muscle and may be one of the causes for urgency. Urinary incontinence refers to a condition of involuntary loss of urine, and may include urge incontinence, stress incontinence, or both stress and urge incontinence, which may be referred to as mixed urinary incontinence.

Although the techniques primarily described in this disclosure are for treating bladder dysfunction, the techniques may also be applied to treat other pelvic floor dysfunctions or disorders relating to other organs of the patient. For example, the devices, systems, and techniques described in this disclosure alternatively or additionally may be utilized to treat pelvic pain or other pelvic floor pathologies including, for example, irritable bowel syndrome (IBS), fecal urgency, fecal incontinence, and sexual dysfunction.

Moreover, while the techniques are primarily described with regard to delivery therapy to C fibers in a manner that at temporarily deactivates the C fibers to treat pelvic dysfunction and/or pain, such techniques may be applied to any nerve fiber, including group A, B and/or C fibers. In some examples, the nerve fibers are unmyelinated nerve fibers. In other examples, the nerve fibers may be myelinated nerve fibers. The nerve fibers may be targeted individually or in the form of a bundle of such nerve fibers. The therapy delivered to the nerve fiber(s) may temporarily damage or permanently damage the nerve fiber(s) such that the nerve fiber(s) are temporarily or permanently deactivated (e.g., no longer firing) by the therapy to treat pelvic floor dysfunction and/or pain.

Sensory nerves may include large myelinated Aβ (A-beta) fibers, small myelinated Aδ (A-delta) fibers and unmyelinated fiber, such as, e.g., C fibers. Both Aδ fibers and unmyelinated C fibers are reported as innervating the urinary bladder. C fibers in the bladder are thought to be inactive under normal condition, and respond primarily to chemical irritation, thermal stimuli and noxious stimuli. The fibers may acquire mechanical sensitivity and become activated in pathological states such as neurogenic detrusor overactivity. An abundance of the suburothelial sensory nerves may serve to increase the sensation of bladder filling leading to overactive bladder symptoms.

As described in this disclosure, various techniques and systems may be used to reduce or otherwise manipulate group C fiber nerve activity and/or activity of other nerve fibers (e.g., unmyelinated nerve fiber(s)) in a patient to treat one or more pelvic disorders and/or pain of a patient. Such example techniques may include delivery of therapy to group C fibers and/or other nerve fibers (e.g., unmyelinated nerve fiber(s)) in the pelvic floor, suburothelium, bladder wall of a patient, and/or in the sacral nerve. The therapy may be delivered to group C fibers and/or other nerve fibers (e.g., unmyelinated nerve fiber(s)) on a unilateral or bilateral basis. In some examples, the nerve fibers may be located in the pelvic nerve branches, e.g., individually or as part of a bundle of nerve fibers. In such examples, C-fiber afferents may exhibit spontaneous firing when the bladder is empty and increase firing (e.g., in terms of frequency) during bladder distension. Some mechanical silent C fibers become mechanosensitive, e.g., susceptible to being deactivated (temporarily or permanently) by the application of mechanical force, e.g., due to damage to the nerve fiber from the application of force.

In some examples, one or more particular C fibers in a patient may be identified to target with therapy that deactivates those particular C fibers, e.g., on a temporary or substantially permanent basis. For example, anatomical regions that are densely innervated, such as, e.g., trigone and/or suburothelial layers, may be identified based on the likelihood of nerve fibers being present. In one example, one or more C fibers may be identified by distinguishing one or more C fibers from other nerves or tissue that does not include C fibers. In this manner, delivery of therapy to non-C fiber sites may be prevented.

As another example, one or more techniques may be used to identify C fibers that exhibit nerve activity that is associated with pathological manifestations of a pelvic floor disorder of a patient which is the target of the treatment. In one example, in the case of bladder dysfunction, the identified C fiber nerve activity may be nerve activity that is observed when the bladder of a patient is substantially empty or only partially filled, e.g., as determined based on patient input and/or via a medical device using any suitable bladder level sensing technique. This nerve activity may be sensed and recorded by a medical device and used to identify nerve fibers to target for therapy and/or determine whether or not a therapy was successful in at least temporarily deactivating the nerve fibers. The nerve activity may be accompanied by undesired contraction of the bladder, bladder voiding, and/or pelvic pain. Thus, it may be desirable to deactivate such C fibers to prevent future activation of the C fibers when the bladder is substantially empty or only partially full.

By identifying undesired C fiber activity, a therapy may be targeted for the identified C fibers rather than C fibers or other nerve fibers that do not cause one or more undesirable symptoms or manifestations of that pelvic floor dysfunction that is being treated. In this manner, the damage to other C fibers or other nerve fibers caused by the therapy delivered may be reduced or eliminated while still treating the pelvic floor disorder by deactivating the C fibers causing one or more of the undesirable symptoms or manifestations of that pelvic floor dysfunction.

A medical device (e.g., an external, surgical, and/or implantable medical device) may be used to deliver therapy to at least a portion of one or more C fibers to deactivate those C fibers. As described herein, in some examples, the therapy may be delivered to portions of one or more C fibers to deactivate the C fibers such that the C fibers are no longer functionally firing or otherwise permanently destroyed. The therapy may be delivered as an acute basis rather than a chronic basis. As an example, the therapy may include the ablation and/or mechanical stretching or other mechanical application of force of one or more portions of a C fiber or bundle of C fibers to deactivate the one or more of the C fibers during a surgical procedure as compared to, e.g., an electrical stimulation therapy that may be delivered to patient substantially continuously on a chronic basis to manage patient pain or a patient disorder.

While the therapy delivery may be delivered to a patient on an acute basis, the deactivation of the C fiber(s) resulting from the therapy may last after the therapy is no longer actively being delivered, e.g., after the C fibers are no longer being ablated or the C fiber is no longer being stretched. In some examples, the C fibers subject to the therapy may be permanently deactivated. Conversely, in other examples, the C fibers may only be deactivated temporarily (e.g., for weeks, months, or years) based on a number of factors including the regeneration of the C fibers that have been deactivated by the delivered therapy. In such examples, therapy may be delivered on a periodic basis (e.g., weekly, monthly, or yearly) to manage the pelvic floor disorder treated by the C fiber deactivation. In some examples, the acute therapy may be re-delivered to the patient once the C fibers deactivated by the therapy are reactivated (e.g., resume exhibiting nerve activity) to once again deactivated the C fibers. In other examples, the acute therapy may be re-delivered periodically prior to the deactivated C fibers reactivating to maintain the C fibers in a deactivated state rather than allowing the C fibers to become active prior to redelivering the therapy.

Any suitable type of therapy may be employed to deactivate one or more C fibers in the patient. In some examples, the therapy may include ablation targeted for the identified C fibers. Ablation, as described here, may include any technique that destroys and/or removes all or portions of targeted C fibers. The targeted ablation therapy may ablate portions of the identified nerve fibers instead of other nerve fibers (e.g., other C fibers, A fibers, B fibers, and/or other tissue of the patient). Alternatively, therapy may target one, or a combination of C fibers, A fibers, B fibers, and/or other tissue of the patient. Example ablation techniques may include chemical ablation, radio frequency ablation, ultrasound ablation, mechanical ablation, heat ablation, cold/cyroablation, or other processes for, e.g., damaging targeted C fibers in manner that deactivates the C fibers. Chemical ablation may include the delivery of acid, capsaicin, resiniferatoxin (RTX), botulinum toxin to target C fibers to deactivate the fibers, e.g., by temporarily or permanently damaging the nerve fibers. As C fiber nerve activity may cause one or more undesired symptoms or manifestations of a patient dysfunction, targeted ablation of C fiber in the patient may thus alleviate those symptoms and/or manifestations related to bladder dysfunction or other pelvic dysfunctions associated with the C fiber activity.

Additionally or alternatively, other types of therapy besides ablation therapy may be employed to deactivate target C fibers of a patient in a manner that treats a pelvic floor dysfunction of the patient. For example, as will be described below, it has been found that the mechanical stretching one or more C fibers may successfully deactivate the stretched C fibers. It is believed that the deactivation of C fibers in such a manner may successfully treat bladder dysfunction or other pelvic dysfunction through the deactivation of the C fibers. In some examples, the mechanical stretching may include the stretching of a C fiber or bundle of C fibers, e.g., in a direction substantially parallel to the longitudinal axis of the nerve and/or a direction substantially traverse the longitudinal axis of the nerve. In some examples, stretching the C fiber(s) in such a manner may effectively destroy or damage the C fibers to a degree that prevents C fibers from firing or responding to bladder filling, e.g., on a temporary basis.

Any suitable device may be used by a clinician to stretch one or more target C fiber in such a manner, such as, e.g., one or more medical pincers to secure and stretch the C-fiber(s) and surrounding tissue. A medical device including a strain gauge configured to measure the amount of strain applied to the nerve fiber (and other surrounding tissue) during the stretching. One or more others technique for applying mechanical force other than stretching may be employed to effectively destroy or damage the C fibers to a degree that prevents C fibers from firing or otherwise deactivating the nerve fiber. For example, a nerve fiber may be compressed, constricted, severed, surgically removed, vibrated, and the like to apply mechanical force to the nerve fiber that damages the nerve fiber as described herein. The stretching and/or other application of force may be apply once (e.g., stretched only once for a given duration of time) or repeatedly (e.g., stretched multiple time for a given duration of time).

The targeted portion of a C fiber may be located outside the tissue of the bladder or other organ. For example, the portion of a C fiber targeted for ablation, stretching, or other therapy to damage or otherwise deactivate the C fiber may be located outside bladder tissue (e.g., bladder wall). In some examples, spot tissue ablation of nerve terminals inside bladder tissue does not work well. It may be more effective to damage nerves from the bundles which could be branches of the pelvic nerve or even spinal nerve e.g. S3, or S1-S3, or dorsal root ganglia.

One or more parameters may be monitored with the delivery of therapy (e.g., during and/or after the delivery of the therapy) to determine if the delivered therapy resulted in the deactivation of one or more of the C fibers. In some examples, a medical device may sense for electrical activity of the C fiber(s) following the delivery of therapy to the patient, e.g., using one or more internal and/or external sense electrodes. In some examples, non-invasive imaging techniques such as magnetic resonance imaging or external electrodes may be used to produce electrograms indicative of the C fiber nerve activity to determine whether or not the delivered therapy has successfully deactivated the target C fiber nerve activity. Such techniques may also be used to initially identify C fibers to target with the therapy delivery.

Additionally or alternatively, the determination may be made based on one or more other parameters indicative of whether or not the C fibers were successfully deactivated by the therapy, such as, e.g., sensed physiological marker(s) of the patient or patient input. Example sensed physiological markers may include bladder impedance, bladder pressure, bowel impedance, bowel pressure, pudendal afferent nerve activity, sacral afferent nerve activity, muscle activity, or motion of the patient. Patient input may include input regarding the presence or absence of one or more symptoms and/or manifestations of the pelvic floor dysfunction being treated, such as, e.g., pain or instances of incontinence.

As will be apparent from the description, examples of the disclosure may provide for delivery of a therapy to the patient to treat pain and/or pelvic floor dysfunction of the patient using a relatively simple and/or minimally invasive therapy, e.g., as compared to other therapy techniques used to treat pain and/or pelvic floor dysfunction with a medical device.

FIG. 1 is a conceptual diagram illustrating an example system 10 configured to ablate targeted portions of C fiber external of bladder 14. However, in other examples, a system may be utilized that is configured to ablate portions of C fibers within the tissue of bladder 14, e.g., via an ablation device that may be inserted into the bladder 14. Ablation, as described here, may include any technique that damages (temporarily or permanently), destroys and/or removes targeted tissue. For example, ablation may include radio frequency ablation, chemical ablation, ultrasound ablation, mechanical ablation, heat ablation, and/or cyroablation individually or in combination.

As shown, system 10 includes ablation device 16, catheter 18, ablation electrodes 20, and handle 22. Ablation device 16 may include a radio frequency (RF) generator that generates the electrical energy delivered to ablation electrodes 20 (e.g., a bipolar pair of electrodes) via conductors housed within catheter 18. In other examples, one or more unipolar electrodes 20 may be used in conjunction with a ground pad or other return electrode. Ablation device 16 may also include a user interface that is configured to receive user inputs controlling ablation device 16 and output an indication of the ablation process, such as the time of ablation, the temperature adjacent ablated tissue, and other related information from one or more sensors 21 carried by catheter 18.

Catheter 18 may be constructed of a biocompatible material and configured to be inserted through an opening 24 in the skin of patient 12 (e.g., via a laparoscopic procedure) and deliver electrodes 20 to the desired tissue location. The distal end of catheter 18 may carry one or more electrodes 20 configured to delivery RF energy to tissue. Electrodes 20 may include one or more surface electrodes (e.g., circular or cylindrical electrodes) that contact a desired tissue and/or one or more electrodes shaped as needles or other elongated shapes configured to penetrate into tissue. Electrodes 20 may be configured to provide bipolar ablation or unipolar ablation. A ground pad may also be electrically coupled to ablation device 16 for the one or more unipolar electrodes 20, and the ground pad may be placed at an external location of the skin of patient 12. Catheter 18 may also include one or more conductors (e.g., wires) that electrically couple each electrode 20 to ablation device 16. Handle 22 may provide a surface to which the clinician can grab and manipulate catheter 18 during ablation.

Although FIG. 1 illustrates catheter 18 accessing nerve fiber 28 anteriorly through an incision in the abdomen of patient 12, any suitable surgically technique may be used to access any target nerve fiber location within patient 12. In some examples, a posterioral approach may be employed. Catheter 18 or other therapy delivery probe may go through small incision on abdominal skin, vagina, colon/rectum (as prostate surgery) or sacral vertebrate foramen. In other examples, the therapy may be delivered non-invasively. For example, a device configured to deliver ultrasound therapy may be located external to patient 12, e.g., on the surface of the upper abdomen of patient 12, and ultrasound energy may be delivered transcutaneoulsy to nerve fiber 28 in a manner that damages the nerve fibers to temporarily or permanently deactivate the nerve fiber 28.

In some examples, catheter 18 may carry additional sensors such as temperature sensors or impedance sensors configured to monitor tissue during ablation. Catheter 18 may also include an optical sensor configured to obtain visual information from the distal end of catheter 18. For example, the optical sensor may provide video information that is displayed to the clinician such that the clinician can navigate electrodes 20 to the appropriate location that correspond to portions of identified C fibers 28 external to bladder 14. Alternatively, catheter 18 may include a channel in which a cytoscope can be inserted to allow the clinician to view tissue at the end of catheter 18.

C fibers 26 and 28 may be located external to bladder 14 and may innervate one or more portions of bladder 14. As described above, such C fibers may exhibit activity that causes one or more pelvic floor dysfunctions such as pain or bladder dysfunction. Therapy may be delivered to one or more portions of one or more of C fibers 26 and/or 28 to deactivate C fibers in a manner that treats a pelvic floor dysfunction of patient 12 associated with such C fiber activity.

For example, a clinician may ablate a portion of C fibers 28 by first inserting the distal end of catheter 18 into patient 12. The clinician may insert catheter 18 through a surgically opened area of skin or various laparoscopic techniques. The clinician may then navigate the distal end of catheter 18 to a portion of C fiber nerve. The clinician may identify the appropriate portion of C fiber via visual identification and/or identification via electrogram, for example. Other identification methods are also possible. Once the clinician has positioned electrodes 20 in contact with the targeted portion of C fiber 28, the clinician may interact with a user interface of ablation device 16 to start delivery of RF energy from ablation device 16 and ablate the portion of the nerve residing external to the detrusor muscle.

Ablation therapy may begin when an RF signal (e.g., RF energy) is transmitted between the two electrodes 20 located at the distal end of catheter 18, e.g., in a bipolar arrangement. Since both of electrodes 20 are in contact with a portion of C fiber 28, this RF signal may increase the heat of fiber tissue adjacent to electrodes 44 until fiber tissue necrosis occurs and ablation of the targeted area is complete. Completion of the targeted ablation of the portion of C fibers 28 may be determined in response to exceeding a threshold temperature of the nerve tissue, exceeding a threshold impedance, or visual confirmation that the nerve tissue has been ablated. In examples in which ablation of multiple portions of one or more C fibers 28 is desired, this process may be iteratively performed at each location.

Although system 10 is described as delivering RF ablation energy, ablation system 10 may be configured to deliver any of the other types of ablation described in this disclosure. For example, catheter 18 may be configured to deliver a chemical to target tissue locations that achieves nerve tissue necrosis. In another example, ablation device 16 may energize one or more ultrasound transducers disposed on catheter 18 that provide ultrasound ablation of the target nerve tissue. In other examples, catheter 18 may carry a heating element that provides heat ablation, carry a nerve tissue removal tool configured to mechanically remove a target portion of C fiber 28, or deliver low temperature fluid configured to provide cryoablation of the nerve tissue. In this manner, system 10 may be configured to provide different types of ablation therapy.

Figure 2:
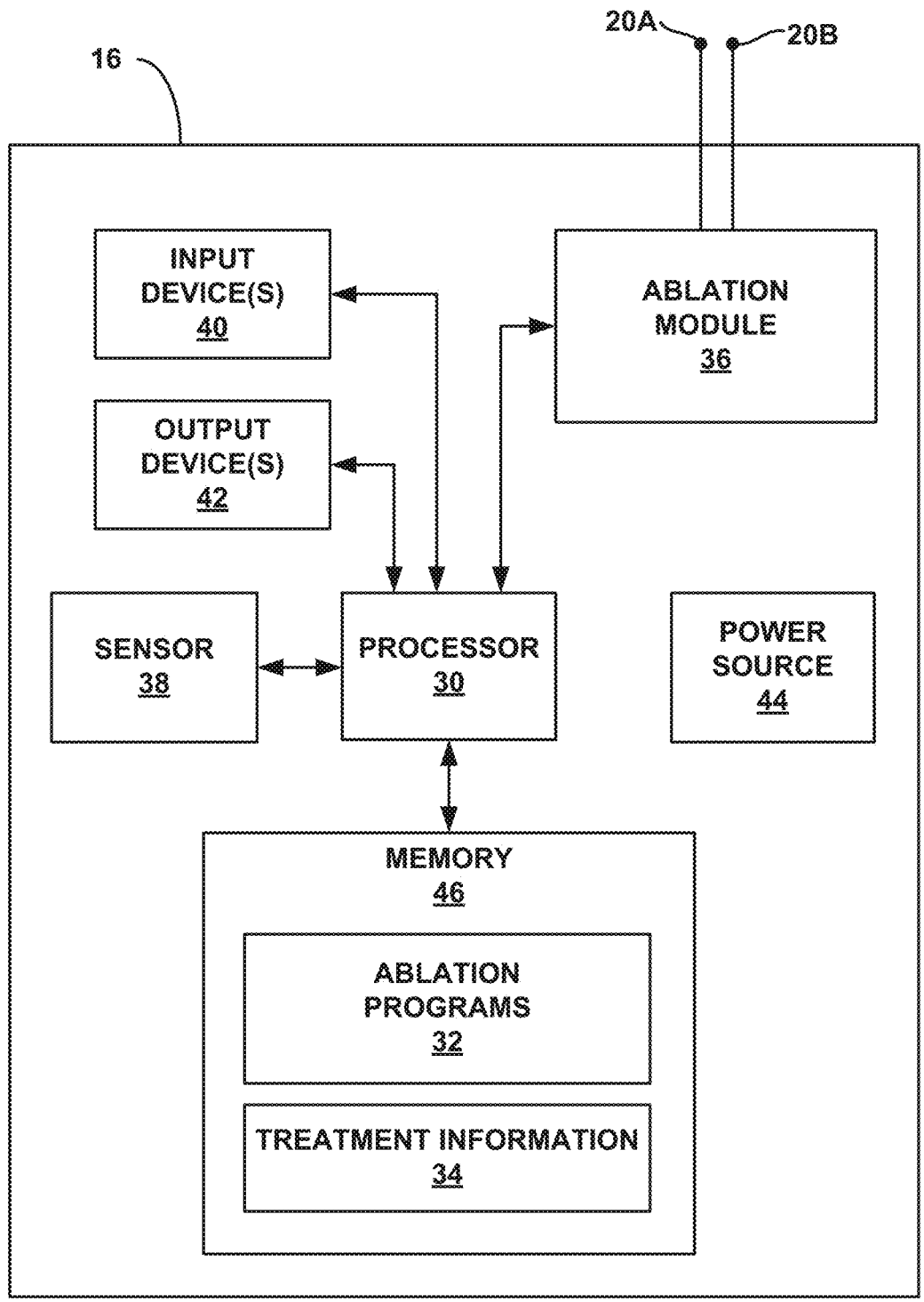
FIG. 2 is a block diagram illustrating an example configuration of an ablation device which may be utilized in the system of FIG. 1.

FIG. 2 is a block diagram illustrating an example configuration of ablation device 16 which may be utilized in system 10 of FIG. 1. In the example of FIG. 2, ablation device 16 includes processor 30, memory 46, ablation module 36, sensor 38, input devices 40, output devices 42, and power source 44. In other examples, ablation device 16 may include more or fewer components. For example, ablation device 16 may include a telemetry module for wirelessly transmitting data or ablation device 16 may not include sensor 38.

Ablation device 16 may comprise any suitable arrangement of hardware, alone or in combination with software and/or firmware, to perform the techniques attributed to ablation device 16 and processor 30 and ablation module 36 of ablation device 16. In various examples, processor 30 of ablation device 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. Ablation device 16 also, in various examples, may include a memory 46, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 30 and ablation module 36 are described as separate modules, in some examples, processor 30 and ablation module 36 (or more devices of ablation device 16) are functionally integrated. In some examples, processor 30 and ablation module 36 correspond to individual hardware units, such as ASICs, DSPs, FPGAs, or other hardware units.

Memory 46 stores information such as data for the operation of ablation device 16 and data generated during the targeted ablation of portions of C fiber 28. Memory 46 may store ablation programs 32 and treatment information 34. Ablation programs 32 may include instructions used by processor 30 to control ablation device 16 to ablate tissue, such as portions of C fibers 28. For example, ablation programs 32 may include instructions for generating an RF signal applied to electrodes 20A and 20B (collectively "electrodes 20") such as ablation parameters. Ablation parameters may include selected electrode configurations, voltage amplitudes, current amplitudes, signal frequency, duty cycles, or any other parameters that define the RF signal. In addition, ablation programs 32 may include thresholds that control the delivery of the RF signal such as temperature thresholds (monitored from a temperature sensor such as sensor 38), time thresholds, impedance thresholds, any other closed-loop or open-loop control mechanisms. Ablation programs 32 may also include algorithms that analyze identified portions of C fibers 28 and generate instructions for the clinician that assist the clinician to selectively ablate the portions of the C fiber that correspond to the identified portions. Ablation programs 32 may additionally include instructions for processor 30 to control input devices 40 to receive user input and output devices 42 to present information to the user. Although ablation programs 32 are described for RF ablation therapy, similar ablation parameters and instructions may be also applicable for controlling different types of ablation therapy such as ultrasound ablation, thermal ablation, mechanical ablation, cryoablation, or any other methods for damaging or removing portions of C fiber(s). Electrical signals may be delivered as electrical stimulation therapy in some examples.

Treatment information 34 may include data generated during the ablation of C fiber(s). Treatment information 34 may include times that ablation therapy was delivered, the number of different locations ablated by ablation device 16, the sensed temperatures of impedances from sensor 38, calculated or detected sizes of ablated nerve tissue, or any other information. Processor 30 may, in some examples, present treatment information 34 to the user via output devices 42 and/or transmit treatment information 34 to another computing device via a communication module (not shown in FIG. 2). Treatment information 34 may also include time and date stamps to indicate when the C fiber was ablated, an indication of the patient that received the ablation, and/or an identity of the clinician that performed the ablation. Treatment information 34 may also include any detected errors that occurred during the ablation process.

Ablation module 36 is configured to generate and deliver ablation energy via electrodes 20. In the example of FIG. 2, ablation module 36 may include an RF signal generator that generates an RF signal transmitted to tissue via electrodes 20. The RF signal may be configured to increase the temperature of tissue and cause the desired ablation of that tissue. Processor 30 may control ablation module 36 or ablation module 36 may include separate processing circuitry configured to control the delivery of ablation energy according to ablation programs 32. Ablation module 36 may be configured to deliver bipolar or unipolar ablation and utilize more than two electrodes in other examples. In examples of ablation device 16 where a different ablation technique is used, ablation module 36 may be configured to generate and deliver the appropriate ablation therapy. For example, ablation module 36 may include circuity configured to module ultrasound transducers for ultrasound ablation or resistively heat elements that provide thermal ablation. In some examples, ablation module 36 may include a pump and conduit that deliver conductive fluid to help distribute RF energy to the tissue. Alternatively, ablation module 36 may include a pump and conduit configured to deliver chemicals that ablate tissue or cryogenic fluid that freeze tissue via one or more catheters terminating at a targeted tissue location.

Sensor 38 may be a temperature sensor that detects the temperature of tissue adjacent to electrodes 20 during the delivery of RF energy. Sensor 38 may receive a signal from a thermocouple, thermistor, or other probe disposed on the catheter also carrying electrodes 20. Processor 30 may monitor the temperature output by sensor 38 and compare the temperature to a threshold. Responsive to determining that the temperature exceeds the threshold, processor 30 may automatically terminate delivery of the RF energy and/or output an alert to be presented to the user via output devices 42. In other examples, sensor 38 be an impedance sensor and may monitor changes in impedance that indicate ablation progress, or any other type of sensor appropriate for the type of ablation being delivered by ablation device 16.

Ablation device 16 may be configured to receive inputs from a user. Input devices 40 may include one or more buttons, keypads, touch-sensitive screen, pointing device, or any other input device. Output devices 42 may include one or more lights, a speaker, and a display, such as a liquid crystal (LCD), light-emitting diode (LED), or cathode ray tube (CRT) display. In some examples the display may be a touch screen. Output devices 42 may thus be configured to output information (e.g., the status of ablation therapy and/or treatment information 34) to a user. Processor 30 may be configured to control input devices 40 and output devices 42. For example, processor 30 may control output device 42 to present a status of current RF energy delivery and/or a temperature of the ablated tissue sensed from sensor 38. Processor 30 may also control output devices 42 to present the previously generated map of identified focal points and update the map as focal points are ablated. In some examples, the combination of input devices 40 and output devices 42 may be referred to as a user interface for ablation device 16.

Although not shown in FIG. 2, ablation device 16 may also include a communication module configured to receive data from another computing device and/or transmit data to another computing device. The communication module may be configured to communicate via wired or wireless communication protocols for direct communication or via a network. Examples of wireless communication techniques that may be employed to facilitate communication between ablation device 16 and another computing device include RF communication according to the 802.11 or Bluetooth specification sets, infrared communication, e.g., according to the IrDA standard, or other standard or proprietary telemetry protocols.

Power source 44 delivers operating power to the components of ablation device 16. Power source 44 may include a battery and a power generation circuit to produce the operating power. In some examples, the battery may be rechargeable to allow extended operation. In other examples, power source 44 may be configured to receive power from an alternating current (AC) outlet.

In some examples, sensor 38 may be configured to sense nerve activity of patient 12 via electrodes and/or other electrodes located externally or implanted in patient 12. The sensed nerve activity may be exhibited by C fibers 28. Based on the sensed nerve activity, ablation device 16 may identify one or more C fibers to target for ablation or other therapy. Following ablation of portions of the identified C fibers, sensor 38 may be used to confirm whether or not the ablation successfully deactivated the target C fibers, e.g., based on whether or not nerve activity of those C fibers is sensed by sensor 38. In some examples, nerve activity sensed via sensor 38 may be used as feedback to modify the location of electrodes and/or one or more parameters defining the ablation of targeted portions of C fiber 28, such as, e.g., temperature, until the ablation successfully deactivates the C fiber activity. Although sensor 38 is shown as a component of ablation device 16, one or more separate sensing device may be used to sense nerve activity of patient 12, e.g., using one or more suitable external or implanted electrodes. Such a sensing device may communicate the sensed nerve activity via wired or wireless telemetry to ablation device 16 and/or present the sensed nerve activity to a clinician for review.

Sensor 38 and/or one or more other sensing devices may be used to sense one or more other physiological parameters of a patient that may be used to determine the success of the ablation therapy in deactivating the targeted C fibers to treat a pelvic floor dysfunction of patient 12 and/or making modification to the ablation therapy. For example, sensor 38 and/or one or more other sensing devices may be configured to sensed physiological markers such as, e.g., bladder impedance, bladder pressure, bowel impedance, bowel pressure, pelvic floor muscle activity, or motion of the patient. Each of the physiological parameters may be indicative of whether or not the target C fiber activity has been deactivated, e.g., based on whether or not an undesired voiding event has occurred or muscle activity associated with C fiber nerve activity is present. In some examples, disease condition markers or nerve injury markers may be monitored to evaluate that success of a therapy. A disease condition marker may be a marker that is indicative of the disease either being treated or not treated (e.g., nerve growth factors, prostaglandins, cytokines). In other example, marker(s) of nerve injury (indicators of whether a nerve injury has taken place) may be monitored such that it may be determined whether or not the therapy successfully damaged nerve fiber(s). Such markers may be present in the blood or urine of a patient or may be indicated by the one or more other monitored patient parameter such as body temperature or tissue temperature.

In some examples, system 10 may include a user interface, such as, e.g., as part of input device 40, that allows a patient or other user to provide input regarding the presence or absence of one or more symptoms and/or manifestations of the pelvic floor dysfunction being treated, such as, e.g., pain or instances of incontinence, to determine whether or not the ablation therapy was successful. The changes in the current perception threshold to electrical stimulation of urethral and bladder (e.g., as described by Kenton K, Simmons J, Fitzgerald MP, et al. Urethral and bladder current perception thresholds: Normative data in women. J Urol 2007; 178:189-92) may also be used to determine C fiber activities (e.g. 5 Hz stimulation vs 250 Hz stimulation of Aδ fiber activation).

Although not shown in FIG. 1, system 10 may alternatively or additionally include a device configured to deliver a therapy to patient 12 other than that of ablation that is configured to deactivate targeted C fibers, such as, e.g., C fibers 26 and 28 of the pelvic floor of patient 12. For example, system 10 may include one or more devices configured to mechanically stretch (once or repeatedly) one or more portions of C fiber 28 in a manner that deactivates C fiber 28. Suitable devices may include medical pincers that may be inserted through opening 24 by a clinician to access, secure and stretch a targeted portion of C fiber 28 until C fiber 28 has been deactivated. The physician may attach the device to targeted tissue at two locations proximate C fiber 28. One or both attached sides of the device may be moved to stretch the one or more portions of C fiber 28. In some examples, a device may include a strain gauge or other gauge to measure the amount of strain or other force applied to C fiber 28 as well as a timer to determine the duration that the force was applied. In one example, nerve fiber 28 may be stretched by mechanically separating the nerve fiber (e.g., by pulling) from surrounding fatty tissue, e.g., using any suitable instrument.

As another example, system 10 may include a device configured to deliver a therapeutic agent or other chemical to patient 12 to deactivate C fiber 28. For example, system 10 may include a syringe that may be used to inject a desired substance in fluid for to one or more target sites in patient 12 to deactivate one or more C fibers in or near the pelvic floor in a manner that treats a pelvic dysfunction of patient 12. As another example, system 10 may include an implantable or external fluid delivery device including a catheter that delivers a therapeutic fluid to one or more locations within patient 12 that deactivates one or more C fibers in or near the pelvic floor in a manner that treats a pelvic dysfunction of patient 12. Example therapeutic agents that may be employed to successfully deactivate C fiber 28, for example, may include capsaicin, resinferatozin, RTX, and botulinum toxin. However, other therapeutic agents are contemplated.

Figure 3:
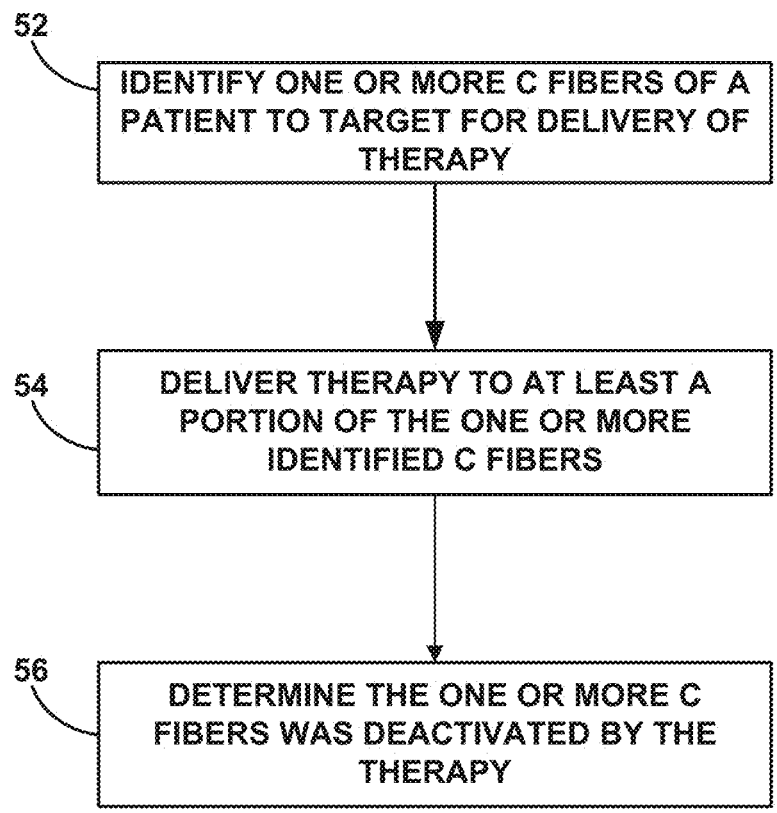
FIG. 3 is a flow diagram that illustrates an example technique for treating pelvic floor dysfunction of a patient, according to one or more aspects of the disclosure.

FIG. 3 is a flow diagram that illustrates an example technique for treating pelvic floor dysfunction of a patient, according to one or more aspects of the disclosure. For ease of illustration, the technique of FIG. 3 will be described as being carried out by system 10 of FIG. 1. However, the example technique of FIG. 3 may be carried out using any system suitable for performing such a technique. In other examples, the technique of FIG. 3 may be directed to different types of nerve fibers instead of, or in addition to, C fibers.

As shown in FIG. 3, ablation device 16 may be used to identify one or more C fibers, such as, C fiber 20 of patient 12 adjacent to bladder 14, to target for delivery of therapy (52). In one example, activation of C fiber may cause one or more undesired symptoms or manifestations of a pelvic floor dysfunction of patient 12. In some examples, sensor 38 may sense nerve activity and processor 30 may identify C fiber 20 based on the sensed nerve activity. One or more other suitable techniques may additionally or alternatively be employed including, but not limited to, visual identification of the C fibers, e.g., using a cytoscope or other imaging device on the end of ablation device 16, or identification of the C fibers based on anatomical location within patient 12.

In some examples, the identification C fibers may include distinguishing the C fibers from other types of nerve fibers and/or other non-nerve fiber tissue. In other examples, the identification may include identifying C fibers that exhibit activation associated with associated with pathological manifestations of a pelvic floor disorder of a patient which is the target of the treatment. For example, in the case of bladder dysfunction, system 10 may sense C fiber nerve activity and monitor the fill level of bladder 14 to identify nerve activity that is observed when the bladder of a patient is substantially empty or only partially filled. The nerve activity may be accompanied by undesired contraction of the bladder, bladder voiding, and/or pelvic pain. Based on the temporal association, the C fibers exhibiting such pathological activations may be identified as a target for the delivery of therapy to deactivate the C fiber. In this manner, the C fibers causing undesired symptoms or manifestations of the pelvic floor disorder may be targeted rather than C fibers or other nerve fibers/tissue that do not cause one or more undesirable symptoms or manifestations of that pelvic floor dysfunction that is being treated.

Ablation device 16 may then deliver therapy to one or more portions of the identified C fiber 20 of patient 12 to deactivate the identified C fiber (54). The therapy may include the ablation of at least a portion of the identified C fiber using on or more of the ablation techniques described herein. Alternatively or additionally, non-ablation techniques such as, e.g., mechanical stretching, may be employed as the therapy delivered to the identified C fiber in a manner that deactivates the C fiber. Such therapy may be delivered to one or more target sites of a C fiber or multiple C fibers.

C fibers are unmyelinated and not "protected" from stretching. Put another way, C fibers or other unmyelinated fibers may be more easily damaged by the application of stretching or other mechanical force, e.g., as compared to myelinated fibers. For example, less force may be required to damage unmyelinated fibers compared to myelinated fibers in a manner that deactivates the fibers. C fibers are also relatively sensitive and easy to damage by thermal ablation or chemical ablation. For example, C fibers are highly expressed with TRPV1 channel (mechanosensitivity), TRPM8 channels (cold sensitivity), TRPV1 channels (heat sensitivity or sensitive to acid, or capsaicin). Bladder hyperactivity is associated with increased excitability of those channels/receptors. Though it is not clear whether the high expression of those channels would lead to high frafigibilty of nerve injury to mechanical, thermal and chemical manipulation, in some examples, evidence does suggest that overactivation of TRPV1 channels by capsaicin or resiniferotoxin will at least temporarily damage C fibers.

In the example of application of mechanical force, any suitable amount of force may be applied that damages the nerve fiber in a manner that at least temporarily deactivates the nerve fibers. In some examples, a force of at least 0.3 Newtons (N), such as, e.g., at least 0.4 N, at least 0.5 N, at least 1 N, at least 10 N, at least 20 N, at least 100 N, at least 200 N, at least 300 N, at least 400 N, at least 500 N, at least 600 N, at least 700 N, or at least 800 N (all values are approximate) may be applied (e.g., via stretching). The force may be applied for any suitable duration such as, e.g., 0.1 seconds, 0.5 seconds, 1 second, 10 seconds, 30 second, one minute, two minutes, 10 minutes, one hour (all values approximate) on an individual or repeated basis.

Following the delivery of therapy to the C fiber, ablation device 16 may be used to determine that the C fiber was successfully deactivated by the therapy (56). For example, sensor 38 may be employed to sense if pathological nerve activity used to identify the targeted C fiber is still be exhibit. If such nerve activity is no longer being exhibited, the therapy delivered to the identified C fiber may be determined to be a success. Additionally or alternatively, one or more other parameters may be used to determine whether or not the therapy was successful in deactivating the identified C fiber(s). For example, as described above, sensor 38 and/or one or more other sensing devices may sense physiological markers such as, e.g., bladder impedance, bladder pressure, bowel impedance, bowel pressure, pelvic floor muscle activity, or motion of the patient. Each of the physiological parameters may be indicative of whether or not the target C fiber activity has been deactivated, e.g., based on whether or not an undesired voiding event has occurred or muscle activity associated with C fiber nerve activity is present. In some examples, system 10 may receive input from a user indicating whether or not one or more symptoms and/or manifestations of the pelvic floor dysfunction being treated, such as, e.g., pain or instances of incontinence, is present or absent since the therapy delivery to determine whether or not the ablation therapy was successful at treating or alleviating one or more symptoms of the dysfunction.

As described above, the therapy delivered by system 10 may be an acute therapy that does not need to be delivered on a continuous or substantially continuous basis to deactivate the C fiber in a manner that treats the patient dysfunction. However, as noted above, the C fibers may only be deactivated temporarily (e.g., for weeks, months, or years) by the therapy based on a number of factors including the regeneration of the C fibers that have been deactivated by the delivered therapy. In such examples, the acute therapy process of FIG. 3 or other such acute therapy may be delivered on a periodic basis (e.g., weekly, monthly, or yearly) to manage the pelvic floor disorder treated by the C fiber deactivation. In some examples, the acute therapy may be re-delivered to the patient once the C fibers deactivated by the therapy are reactivated (e.g., resume exhibiting nerve activity) to once again deactivated the C fibers. In other examples, the acute therapy may be re-delivered periodically prior to the deactivated C fibers reactivating to maintain the C fibers in a deactivated state rather than allowing the C fibers to become active prior to redelivering the therapy.

Figure 4:
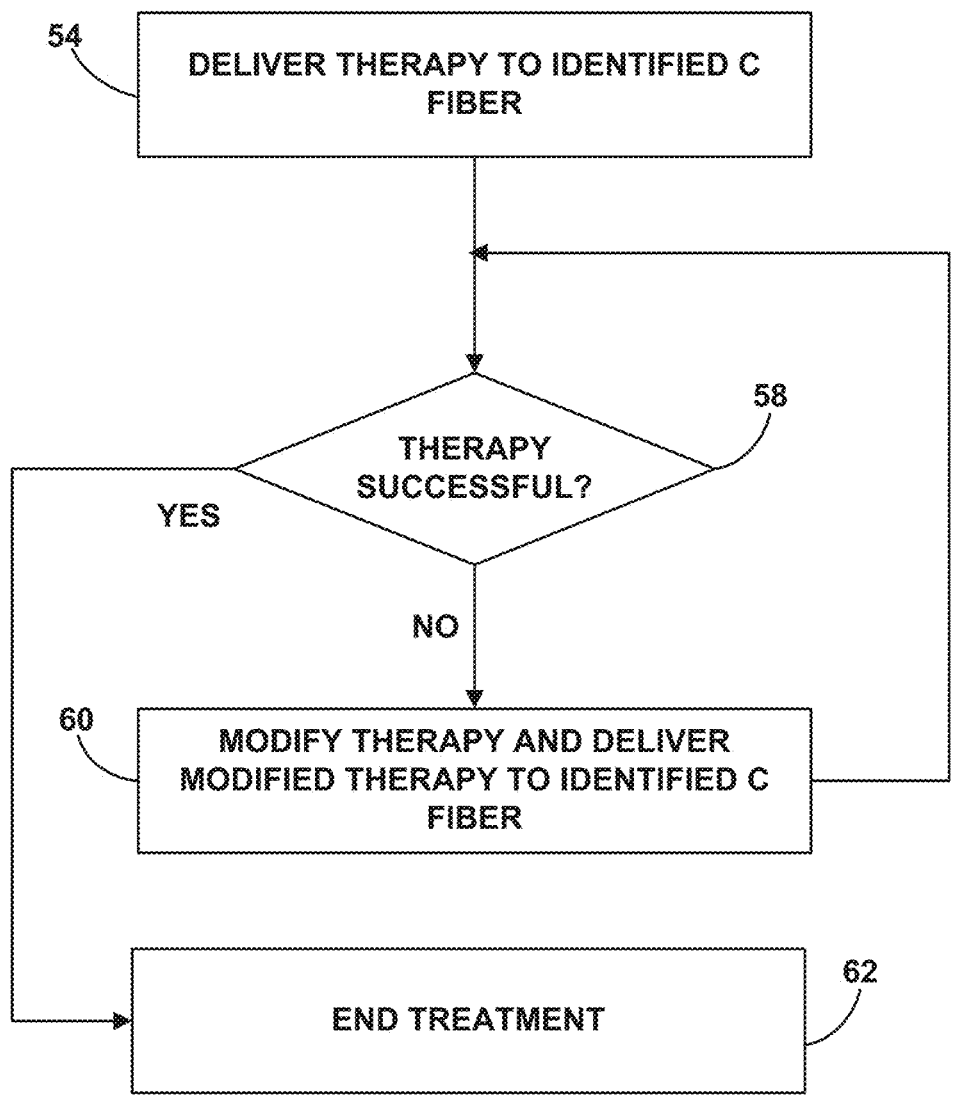
FIG. 4 is a flow diagram that illustrates an example technique for treating pelvic floor dysfunction of a patient, according to one or more aspects of the disclosure.

FIG. 4 is a flow diagram that illustrates an example technique for treating pelvic floor dysfunction of a patient, according to one or more aspects of the disclosure. For ease of illustration, the technique of FIG. 4 will be described as being carried out by system 10 of FIG. 1. However, the example technique of FIG. 4 may be carried out using any system suitable for performing such a technique. The technique of FIG. 4 may be employed for the therapy delivered to patient 12 as described with regard to the process of FIG. 3.

As shown in FIG. 4, ablation device 16 may deliver therapy to one or more portions of an identified C fiber 20 of patient 12 to deactivate the identified C fiber as described above with regard to FIG. 3 (54). System 10 may then be used to determine whether or not the delivered therapy was successful in deactivating the C fiber (58). Any suitable technique may be used to make such a determination including those examples described above with regard to FIG. 3. If the therapy is determined to be successful ("YES" branch of block 58), the treatment of the patient may be ended (62).

Conversely, if the therapy is determined to be unsuccessful ("NO" branch of block 58), the therapy may be modified and then re-delivered to the patient 12 (60). The therapy may be modified, for example, by adjusting one or more parameters defining the originally delivered therapy. In terms of ultrasound, thermal ablation, and cryoablation, example parameters may include temperature during the therapy and/or length of time at which the temperature is applied. The therapy may also be modified by changing the particular target location to which the therapy is being delivered. In the example of mechanical stretching, the therapy may be modified, e.g., by adjusting the amount of force and/or strain being applied to stretch the C fiber and adjacent tissue. In the example of chemical therapy, the dose of chemical delivered and/or type of chemical being deliver during the therapy may be adjusted. In other examples, the actual type of therapy may be adjusted, e.g., to thermal ablation from mechanical stretching. Such an iterative process may be employed until it is determine that a delivered therapy has been successful at which time the treatment of patient 12 may end.

The techniques described in this disclosure, including those attributed to ablation device 16 and system 10, for example, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

EXAMPLE

An experimental study involving anesthetized rats was performed to evaluate one or more aspects of the disclosure. Details of the study are described below and may illustrate one or more aspects of this disclosure.

In the study, rat bladders were infused with 0.3% acetic acid to create an irritation-based model of overactive bladder (OAB). As described below, it was found that mechanically stretching/manipulating pelvic nerves increased bladder capacity (e.g., in term of intercontraction interval (ICI)) and voiding volume (VV) selectively in cystitis rat while C fibers are activated (firing). However, the manipulation did not change bladder function in naïve rats.

Abstract

Aims:

Hypersensitive bladder is a condition in which increased bladder sensations (e.g. urgency, frequency, and pain) are associated with the hyperactivity of bladder sensory fibers in the pelvic nerve (PN). In the study, the potential application of partial bladder denervation (PBD) on attenuation of the hypersensitive bladder was evaluated using cystometry in a rat model of cystitis.

Methods:

In normal rats (n=16) and in rats with cystitis induced by intravesical infusion of 0.3% acetic acid (a.a) (n=26), cystometry was evaluated under urethane anesthesia (i.p. 1.4 g/Kg). The cystometric parameters including intercontraction interval (ICI, min), infused volume (IV, ml), void volume (VV, ml), void duration (VD, second), threshold pressure (TP, mmHg), basal pressure (BP, mmHg) and maximum pressure (MP, mmHg), were compared in rats received no PN manipulations (referred to as naive) or PBD, which was induced by mechanical stretch bilaterally.

Results:

In saline infused rats, PBD (n=8) did not produce changes in cystometry parameters as compared to naïve rats (n=8). The IV and VV were 0.58±0.06 and 0.59±0.07, and 0.65±0.09 and 0.68±0.11, respectively (P>0.05, ANOVA). However, acetic acid induced bladder hyperactivity was associated with a significantly lower ICI (3.20±0.59 vs, 13.01±1.64, saline rats, p<0.05, ANOVA, Tukey's posttest). The hypersensitive effects induced by acetic acid were significantly reversed by PBD (n=18) with IV and VV of 0.36±0.04 and 0.38±0.04, which were significantly higher than that in naïve acetic acid-induced cystitis rats (0.16±0.03 and 0.18±0.05, n=8, p<0.05, ANOVA, Tukey's posttest). Other void functions were not impacted as VD, BP, and MP were unchanged by PBD. Among 18 PBD cystitis rats, 7 were measured with cystometry and the observed inhibitory effect of PBD lasted for 3 hrs. The remaining 11 rats received successive PN transection (unilaterally, followed by bilaterally). Unilateral PN transection produced total incontinence (no voiding reflex) in one rat and partial incontinence in 3 rats. In addition, unilateral PN transection produced an immediate inhibition on bladder afferent function, increasing the IV, from 0.42±0.05 to 0.74±0.08 (p<0.05, paired t-test), and threshold pressure, from 28±2 mmHg to 30±2 mmHg (p<0.05). However the efferent voiding function was decreased as reflected by mismatch of the VV (0.43±0.1 ml) and IV (0.74±0.1 ml, p=0.03, paired t-test) and increase in the VD from 38±7 to 95±30 (p<0.05). Bilateral PN transection abolished voiding in all rats.

Conclusions:

PBD selectively inhibited the hypertensive bladder effects in a rat model of cystitis induced by acetic acid. The ability of PBD to influence bladder function depended on the presence of bladder irritation. It is possible that primary C afferent fibers may be more sensitive to mechanical stretch and targeted by PBD.

Materials and Methods

Male Sprague-Dawley rats (n=42) weighing 200-300 g were anesthetized with urethane (Sigma-Aldrich, St. Louis, Mo.; i.p. 1.4 g/kg). Anesthetized rats were maintained at 37° C. with a heating pad (COAX-3T, Viking Medical, Medford Lakes, N.J.) during the studies and were euthanized by CO2 asphyxia upon completion of the experiment. The experimental protocols were approved by the Institutional Animal Care and Use Committee of Medtronic (Minneapolis, Minn.).

An abdominal incision was made to provide access to the urinary bladder. A catheter (PE-50) was inserted into the bladder through a small incision in the apex of the dome and secured using a purse string suture. The other end of the catheter was externalized and the skin incision was closed with suture.

Naïve rats received no PN manipulations. PBD rats received PN mechanical stretches bilaterally. The testis, vas deferens, and seminal vesicle were identified and temporally lifted outside the abdomen to leave enough space for PN isolation. The prostate lobe was reflected laterally to access the major pelvic ganglion and PN. The PN was isolated from the surrounding fatty tissues using 4-6 gentle manipulations (in a scrubbing manner) along the nerve longitudinally with a cotton-tipped applicator. The tip of a curved tweezer #5 (item number: 500232, available from World Precision Instruments Inc. Sarasota, Fla.) then was placed under the PN perpendicular to the PN and was let open by its own force for two times. The force of the tweezer tip was later measured by a Chatillon DEG Force Gauge. The average of 5 measurements was 73.48±2.98 g. In 11 rats, monofilament non-absorbable suture (size 5/0) were preplaced under the isolated PN for future complete successive PN transection. The hypogastric nerves were untouched. Then testis, vas deferens, and seminal vesicle were sent back to the abdomen and the skin incision was sutured shut.

Following surgery, rats were placed in restraints (Braintree Scientific) located above an electronic balance positioned to measure voided urine volume. Urinary bladder catheters were connected to a pressure transducer and an infusion pump (Harvard Instruments) via a three-way connector. Bladder pressure was viewed and recorded via Chart software through a PowerLab data acquisition system (ML880/P, AD Instruments). Bladders were continuously infused with room temperature saline (n=16), or 0.3% acetic acid (irritating the bladder to induce cystitits, n=26) at a rate of 50 $\mu L \cdot min^{-1}$ for the duration of the studies. A 2-hour (hr) infusion was used as an equilibration period allowing bladder parameters to stabilize. After equilibration, a 3-hr cystometry was obtained. Eleven cystitis PBD rats received complete successive PN transection unilaterally using preplaced silk threads after a 30-minute control period. Following 2-hr cystometry under unilateral PN transection, the rats were further received a second PN transection (to achieve bilateral). Cystometry was continually assessed for an additional 30 min.

Figure 5A:
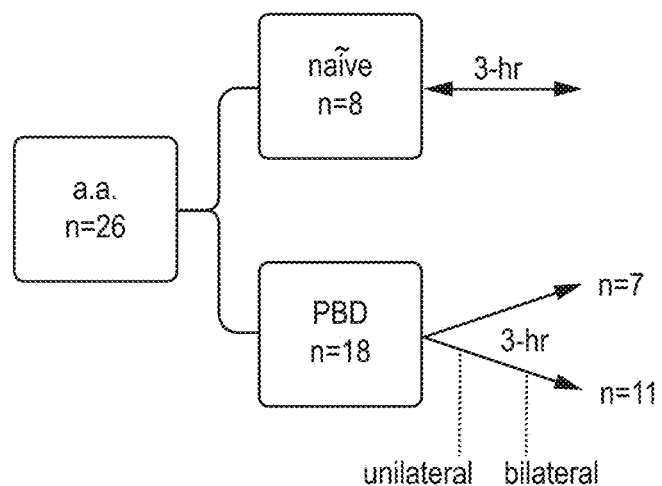
Figure 5B:
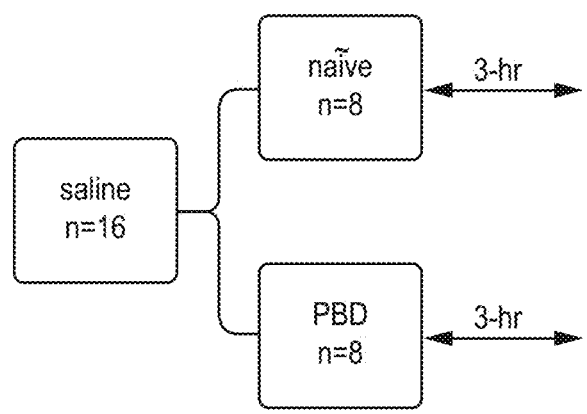
Figure 5C:
Figure 5D:
Figure 5E:
Figure 5F:
Figure 5G:
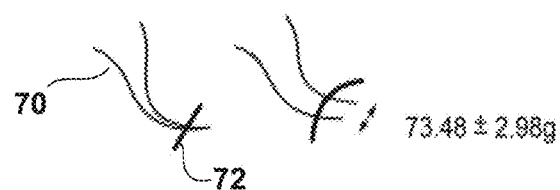

FIGS. 5A and 5B are schematic diagrams illustrating the urodynamic studies in four groups. As shown in FIG. 5A, group 1 included irritated bladder (a.a. infusion) without PBD (naïve, n=8) and group 2 included irritated bladder with PBD (n=18). As indicated in FIG. 5A, among the 18 rats of group 2, 11 were further underwent unilateral and/or bilateral PN transection. As shown in FIG. 5B, group 3 included non-irritated bladder (saline infusion) without PBD (naïve, n=8), and group 4 included non-irritated bladder with PBD (n=8). FIG. 5G is a conceptual diagram illustrating the mechanical stretching that the PBD rats received. As described above, the tip of curved tweezer 70 was placed under the PN 72 perpendicular to the PN 72 and was let open by its own force for two times to stretch the PN.

Data Analysis

Cystometry parameters were assessed including basal bladder pressure (BP, mmHg), maximum pressure (MP, mmHg), threshold pressure (TP, mmHg), void volume (VV, ml), and inter-contraction interval (ICI, min). ICI was measured as the time in minutes between micturition events and VV as the voided volume in mL per micturition event. TP, MP and BP were measured before each micturition occurred, the maximum pressure reached during voiding and after voiding in mmHg. Infused volume (IV) was assessed mathematically as the ICI X 0.05 $\mu L \cdot min^{-1}$ for a given cystometrogram. Data were calculated in 30-minute bins and expressed as averages with associated standard errors. Statistics were performed by using Prism 5 (GraphPad Software, Inc., San Diego, Calif.). One-way ANOVA with Tukey's post-hoc test was used to determine the statistical significance (P<0.05) between different treatment groups and Student t-test was utilized to compare means in prior or post complete nerve transection.

Results

Urodynamic Response Among Different Treatment Groups

In continuous-filling cystometry, measurement of urodynamic parameters during the first 30-min infusion showed a significant difference among the four treatment groups. FIGS. 5C-5F illustrated representative cystometrograms in the first 30 min (a.a. infused groups, FIGS. 5C and 5D) or the first 60 min (saline infused groups, FIGS. 5E and 5F) in the form of raw traces of representative cystometric pressure recording (mmHg).

FIG. 10 is a table ("Table 1") summarizing various cystometry parameters for the rats that received no pelvic nerve manipulations (naive) or partial bladder denervation following intravesical infusion of saline or acetic acid.

Figure 6A:
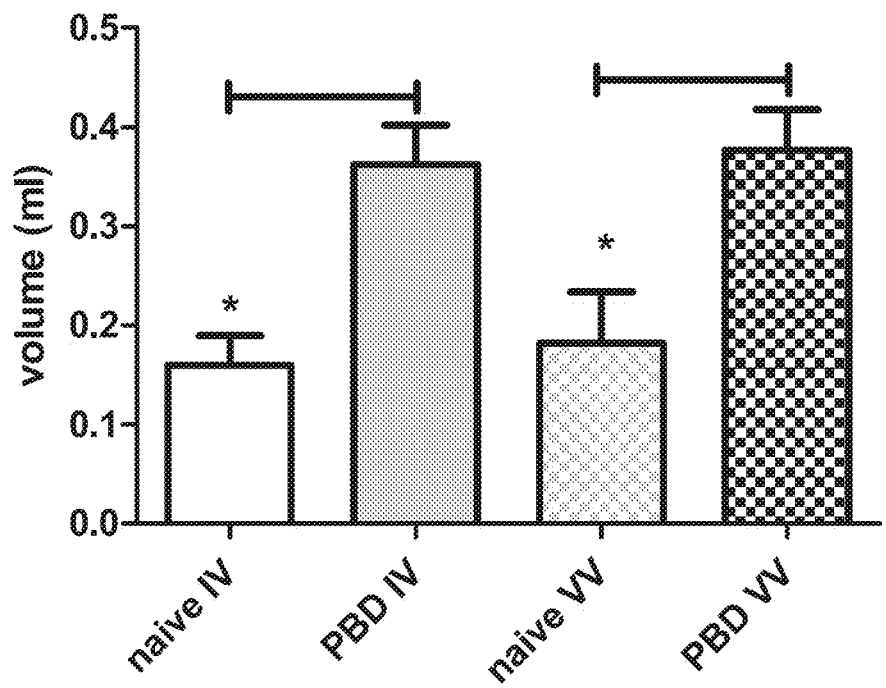
Figure 6B:
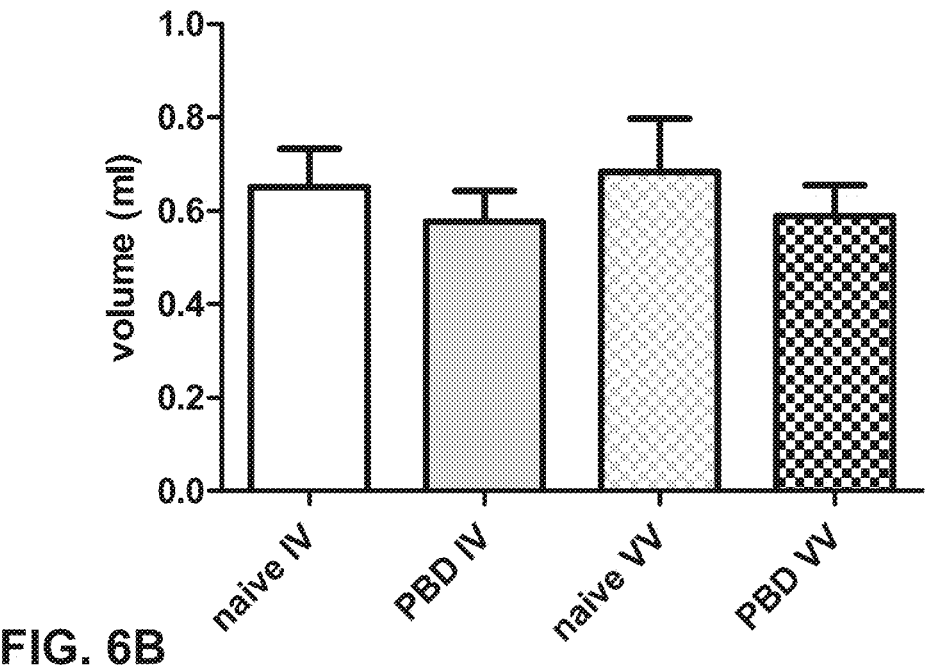

FIGS. 6A and 6B are plots illustrating the urodynamic response of infused volume (IV) and void volume (VV) in naïve rats without nerve manipulation or with partial bladder denervation (PBD). FIG. 6A corresponds to cystometry on cystitis rats induced by intravesical infusion of 0.3% acetic acid (a.a.), and FIG. 6B corresponds to cystometry in normal rats with intravesical infusion of saline. (* p<0.05, ANOVA, Turkey's post test).

Intra-vesical infusion of 0.3% a.a. induced bladder hyperactivity with a significantly lower ICI (3.20±0.59 vs, 13.01±1.64, saline rats, p<0.05, ANOVA, Tukey's posttest, Table 1). There was an increase in BP in a.a. treated rats. One out of 8 cystitis rats had overflow incontinence 2 hours after initiation of a.a. infusion. The hypersensitive bladder effects appeared significantly reversed by PBD (n=18) with IV and VV of 0.36±0.04 and 0.38±0.04, which were significantly higher than that in naïve cystitis rats (0.16±0.03 and 0.18±0.05, n=8, FIG. 2A, * p<0.05, ANOVA, Tukey's posttest, FIG. 6A). BP, TP, MP, and VD were not altered by PBD (Table 1).

In saline infused rats, PBD (n=8) did not produce any changes in the cystometry parameters versus naïve rats (n=8). ANOVA analysis does not demonstrate that a significant change in IV and VV between naïve and PBD rats in saline infused rats (FIG. 6B). The IV and VV were 0.58±0.06 and 0.59±0.07, and 0.65±0.09 and 0.68±0.11, respectively (P>0.05, ANOVA).

Figure 7A:
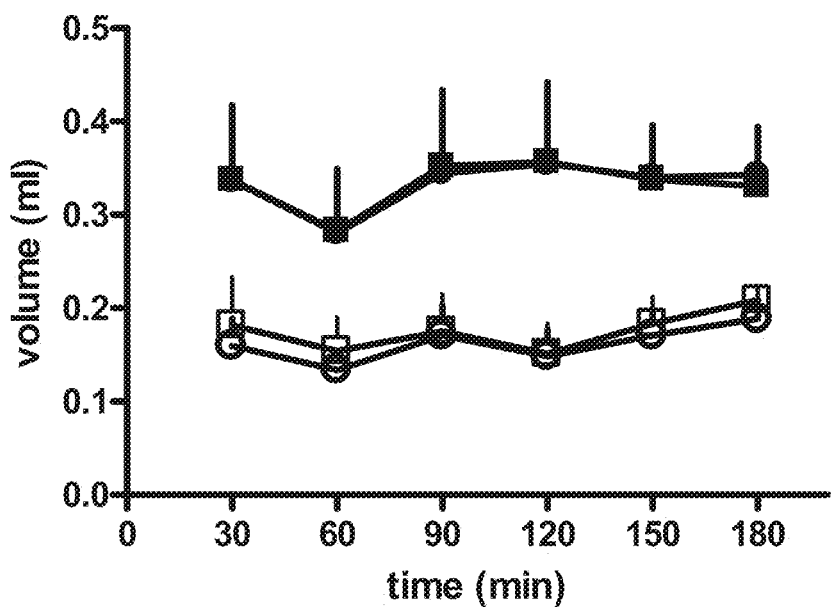
Figure 7B:
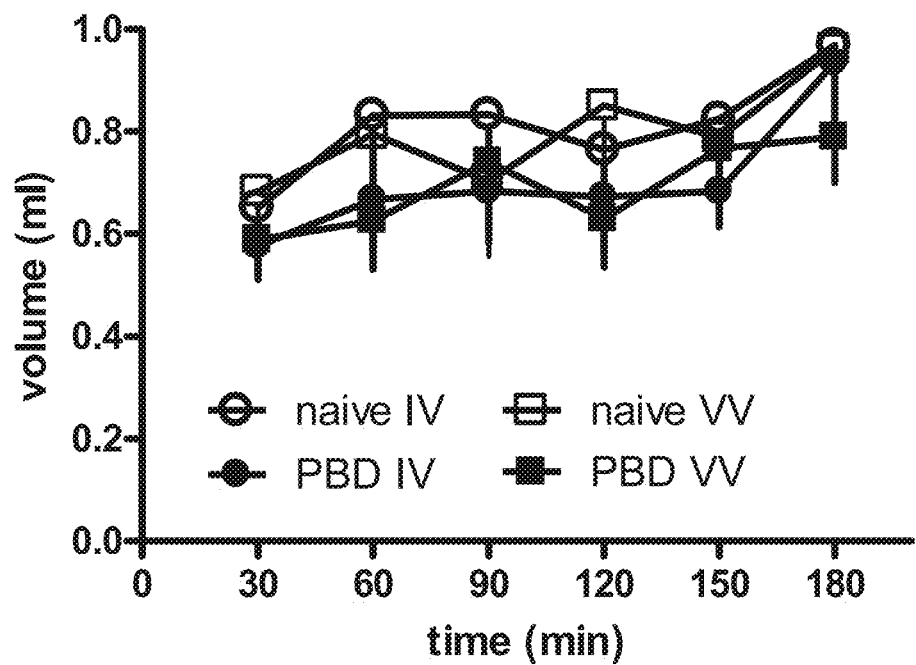

FIGS. 7A and 7B are plots illustrating the time course response of IV and VV among the different treatment groups. FIG. 7A corresponds to the cystometry on cystitis rats induced by intravesical infusion of 0.3% acetic acid (a.a.), and FIG. 7B corresponds to the cystometry in normal rats with intravesical infusion of saline. Among 18 PBD cystitis rats, 7 were observed to demonstrate inhibition of hypersensitive response lasting for 3 hours. As a comparison, the hypersensitive effects evoked by a.a. were also stable over 3 hours of the recording period (FIG. 7A). The IV and VV remained unchanged for at least 3 hours in saline infused rats (FIG. 7B).

Urodynamic Function Following Complete PN Transection

As noted above, among the 18 PBD cystitis rats, 11 rats further underwent unilateral PN transection. One rat was observed to lose the micturition reflex and three rats had urinary incontinence when intravesical pressure had a transitory increase along with a.a. infusion. The remaining 7 rats demonstrated an intact micturition reflex without incontinence in storage phase. Bilateral PN transection abolished voiding in all rats.

Figure 8A:
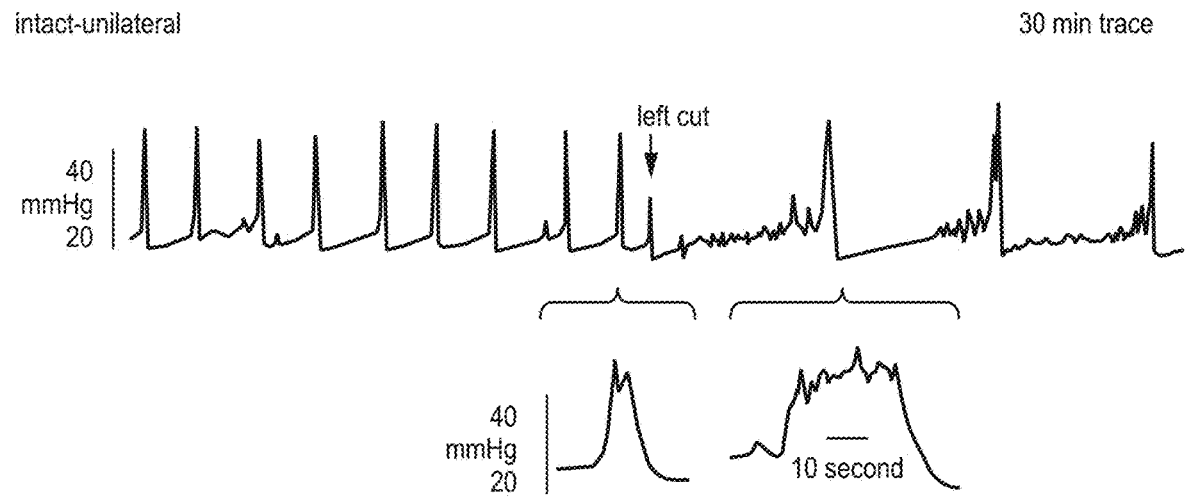
Figure 8B:
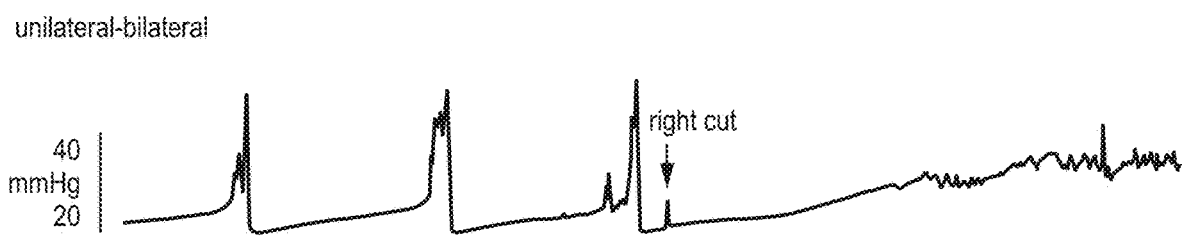

FIGS. 8A and 8B illustrate representative cystometrograms in PBD cystitis rat prior and post whole nerve transection on the left PN (unilateral, FIG. 8A) and consequently on the right PN (bilateral, FIG. 8B). In particular, FIG. 8A corresponds to rats that received a whole nerve transection on the left side of the pelvic nerve (unilateral). Extended displays the single void prior and post unilateral nerve transection were shown below. FIG. 8B corresponds to those rats that, after left nerve transection, consequently received a whole nerve transection on the right side of the pelvic nerve (bilateral).

Figure 9A:
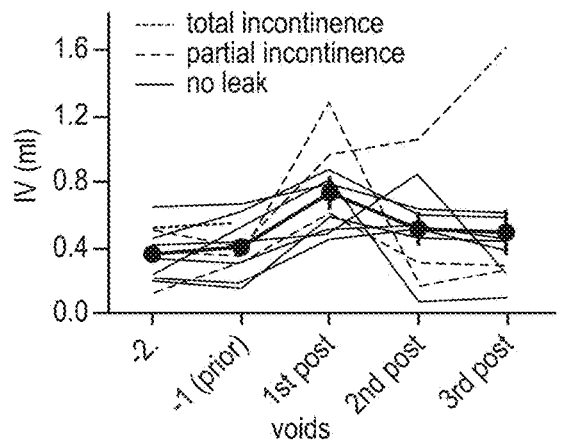
Figure 9B:
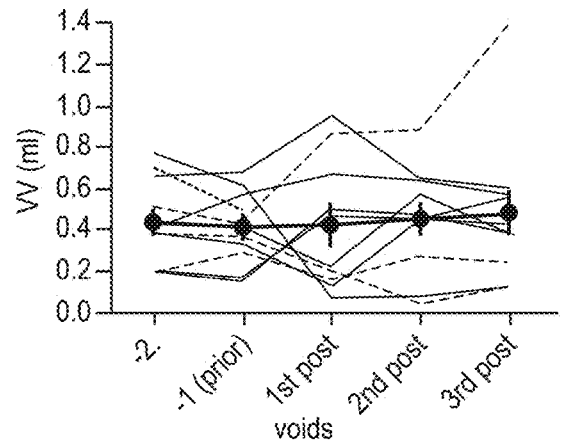
Figure 9C:
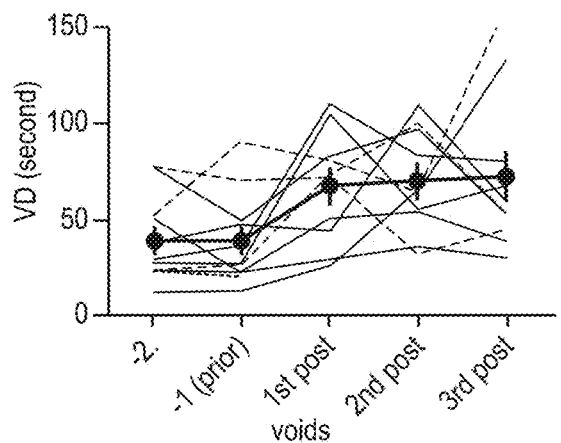
Figure 9D:
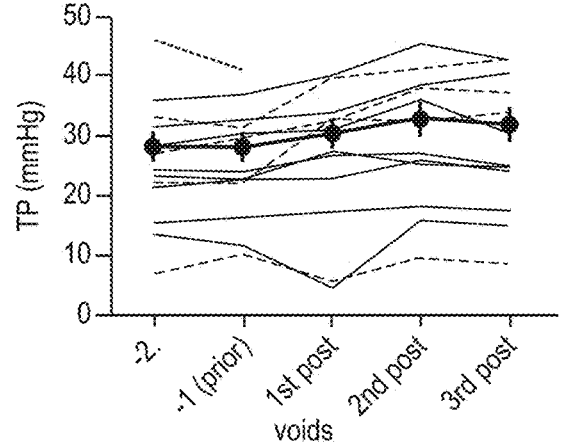
Figure 9E:
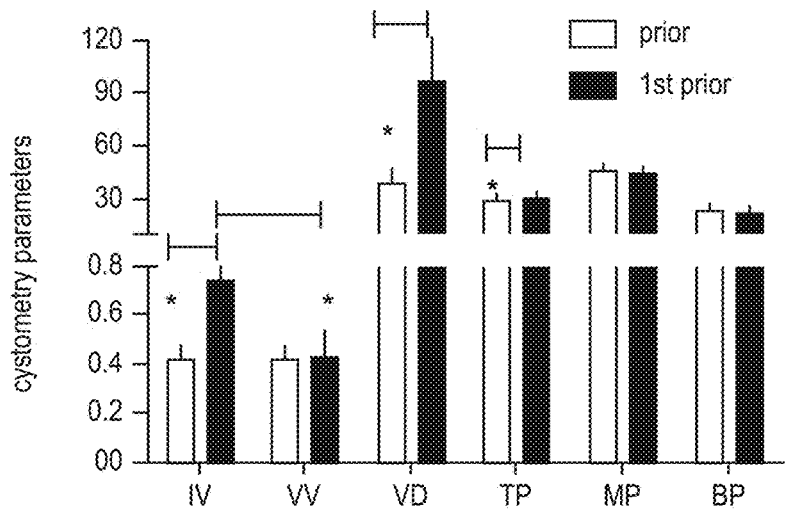

FIGS. 9A-9E are plots showing mean changes in the values of parameters on individual voids prior and post PN transection. FIG. 9A corresponds to IV, FIG. 9B corresponds to VV, FIG. 9C corresponds to VD, and FIG. 9D corresponds to VD of five void cycles (two prior and three post transection) from 11 individual cystitis rats. One rat lost micturition reflex (total incontinence) and three rats had urinary incontinence during a transit increase in intravesical pressure along a.a. infusion (partial incontinence). The remaining seven rats demonstrated an intact micturition (no leak). FIG. 9E is a plot illustrating a comparison of mean changes of the various parameters on the single void prior and post unilateral nerve transection.

Unilateral PN transection produced an immediate attenuation on bladder afferent functions, as indicated by significant increases in IV from 0.42±0.05 to 0.74±0.08 ($p<0.05$, paired t-test), and threshold pressure, from 28±2 mmHg to 30±2 mmHg ($p<0.05$). The increases in IV and TP appeared right after the PN transection, however the increases were diminished following continuous cystometry. The VD increased from 38±7 to 95±30 ($p<0.05$). The VV (0.43±0.1 ml) was not altered to the PN transection. There were no changes in MP and BP in response to unilateral PN transection.

Discussion

The results from the experimental study show that acetic acid may induce bladder hyperactivity with decreases in bladder capacity (lower IV, VV and ICI), a model of cystitis. The results also show that PBD may increase functional urinary bladder capacity in a.a. infused rats. The ability of PBD to influence bladder function appears to depend on the presence of pre-existing bladder irritation. Therefore, the action of PBD appears to be mediated via interference with the peripheral nociceptive pathway.

Animals with experimentally induced cystitis show several sensory and reflex changes that are similar to those seen in humans presenting with cystitis. Based on a previous study, a.a. produced an excitatory effect which stabilized at 2 hours after the beginning infusion and lasted for at least 4 hrs. In the present study, there was a 2-hour equilibration period and data were not recorded during this time, the time course of micturition cycle activation by a.a. was not included. During the 3-hour of recording period, a.a. induced a stable bladder hyperactivity, with a significantly lower ICI, IV and VV, which is consistent with the previous study. The residual volume was not measured. There was an increase in BP which may be an indicator of an accumulation of urine with more residual volume during continuous a.a. infusion. There were no changes in absolute value of the TP, so the value difference from BP to the TP was relatively low. Therefore, in a.a. treated rats, less increase of the intravesical pressure may be required to induce a micturition reflex. Infusion of a.a. into the bladder may induce irritation of the urothelium, stimulate nociceptive afferent fibers and induce an inflammatory reaction. This cystitis model results in a reduction in bladder capacity, a consequent increase in contraction frequency, and other indices of bladder hyperactivity. In the current study, the hyperactivity induced by intravesical administration of a.a. was used to mimic, in the rat, the human condition of detrusor overactivity or bladder hypersensitivity. It is possible that primary C afferent fibers may be more sensitive to mechanical stretch and are appropriate targets of PBD.

The PN innervating the urinary bladder contains both afferent and efferent fibers. Changes in afferent (bladder sensation) and/or efferent activities (bladder contraction) can result in bladder dysfunction. Anatomically it is not clear if the afferent or efferent nerves were injured by mechanical stretch during the study, since both nerves travel in the same bundle. Mechanical stretch used in this experiment is not selective for afferent fibers in the PN. However data that PBD failed to increase basal bladder pressure or decrease the maximum pressure developed during micturition suggests that the PBD does not directly depress the contractility of detrusor smooth muscle. Therefore, inhibition on efferent arm may not be strong enough to impact the contraction during voiding phase. Such effects are similar with the low dose action of antimuscarinic drugs. However, the mechanism that PBD targets efferent nerves/detrusor muscle resulting in a relaxation of bladder smooth muscle and increased bladder capacity cannot be excluded.

The urinary bladder is innervated bilaterally. Removing one side of the PN may reduce bladder afferent signals and parasysmpathetic efferent signals. In PBD cystitis rats, the study found that unilateral PN transection produced an immediate inhibition on bladder afferent function causing increases in the IV and threshold pressure. The increased IV would cause a consequent increase in the VV, and the increased VV would result in an increase in VD. The study found a mismatch following unilateral PN transection, no increase in VV but an increase in VD, along with increased IV, indicating the voiding function was significantly impacted by unilateral PN transection. With the continuous cystometry, the increased IV was soon be masked by large residual volume induced by poor voiding functions.

When the sensory threshold of the bladder fullness was reached as the stretch-sensitive mechanoreceptors of the PN generate maximal afferent signals to the micturition center, the voiding contraction was preceded with a complete relaxation of the urethral sphincter. One of eleven rat was observed to lose the micturition reflex (or voiding contraction was not triggered) to unilateral PN transection. Though the urinary bladder is innervated bilaterally, small population of rats may have unilateral PN dominance. Therefore, the voiding function may be abolished if the dominant PN is transected.

Since the rats were anesthetized, the mechanism that body senses the potential for urine leakage to augment the guarding reflex and prevent unwanted urine loss was missing. Urinary continence would occur when the urethral sphincter activity reaches a peak before the onset of micturition. Three of eleven rats had urinary incontinence when intravesical pressure had a transitory increase along with a.a. infusion, similar with clinical conditions of urinary leakage along with a transitory detrusor contraction. The remaining seven rats demonstrated an intact micturition reflex without incontinence in storage phase.

Bilateral PN transection abolished voiding in all rats. Theoretically this was expected. The results provide confirmation and anatomically accuracy of nerve targeting with PBD.

Several other rat models have been utilized to evaluate the effects of PN on bladder micturition reflex. For instance, acute bilateral pelvic nerve transection has been demonstrated to result in an overflow incontinence and detrusor failure in rats. In a model of peripheral neuropathy mimicking nerve damage during radical pelvic surgery, unilateral pelvic nerves have been transected. Two weeks after unilateral pelvic nerve transection, the maximal intravesical pressure was reduced. No changes occur in the bladder capacity and postvoid residual urine volume.

In our model, PBD produced an acute inhibition on bladder hypersensitivity. Longer term effects following PBD have not been evaluated. Preganglionic whole nerve transection leads to a re-innervation of the cholinergic ganglion by hypogastric nerve in the cats. This could be a phenomenon of nerve regrowth after a loss of the whole nerve. It is unknown if the nerve reorganization would occur following PBD described in this work, but may be evaluated with a histological study and functional study in a longer period of recording. This present study demonstrated the ability of PBD to inhibit elevated bladder activity, although it is not known whether optimal denervation was used for the experimental conditions is applied to clinical conditions.

Finally, if manipulation can be targeted for nociceptive nerve specificity, the "side-effects" on normal bladder function or on other pelvic organs (e.g. colon) will be avoided. Whole nerve transection will impact functions on other pelvic organ functions. Chronically, pelvic nerve transection significantly slows the colonic transit, and shortens the paced mating behavior. However a manipulation on nerves close to the urinary bladder or a gentle nerve manipulation as described in our work would avoid non-target-organ side effects. It was demonstrated that PBD did not change urodynamic function in normal rats. Thus, it is postulated that PBD would not cause sufficient nerve damage to alter normal urinary bladder function.

Based on the study, it appears that PBD by a simple mechanical stretch of the PN may selectively inhibited the excitatory effect induced by a.a. bladder irritation Various examples have been described herein. Any combination of the described operations or functions is contemplated. These and other examples are within the scope of the following claims.

What is claimed is:

1. A medical device comprising:
an ablation catheter device including:
a catheter body;
a handle coupled to the catheter body;
an electrode disposed on a distal end of the catheter body, the electrode designed to deliver an ablation therapy; and
a sensor carried by the catheter body, the sensor designed to sense a patient physiologic parameter,
wherein the ablation catheter device is configured to be used to identify one or more target pelvic nerve fibers of a patient based on nerve activity measured by the sensor at the distal end of the catheter body, and
wherein the ablation catheter device is configured to communicate with a processor, the processor configured to:
cause the ablation therapy to be delivered through the electrode to the one or more target pelvic nerve fibers of the patient to treat pelvic floor dysfunction in the patient, wherein the ablation therapy is configured to at least temporarily deactivate the one or more target nerve fibers,
receive from the sensor a sensed patient physiological parameter following delivery of the ablation therapy, and
determine whether the sensed patient physiological parameter exceeds a predetermined threshold indicative of the one or more target pelvic nerve fibers being at least temporarily deactivated by delivery of the ablation therapy;
wherein the processor is configured to identify the one or more target pelvic nerve fibers based on the nerve activity measured by the sensor at the distal end of the catheter body, wherein the one or more target pelvic nerve fibers is a C fiber that exhibits activation associated with one or more undesirable symptoms or pathological manifestations of the pelvic floor disorder of the patient.

2. The medical device of claim 1, wherein the ablation therapy delivered through the electrode comprises radio frequency ablation therapy.

3. The medical device of claim 1, further comprising a second electrode disposed on the distal end of the catheter body to create a bipolar electrode arrangement.

4. The medical device of claim 1, wherein the patient physiological parameter comprises temperature.

5. The medical device of claim 1, wherein the patient physiological parameter comprises impedance.

6. The medical device of claim 1, wherein the patient physiological parameter associated with the pelvic floor dysfunction is selected from the group consisting of: bladder impedance, bladder pressure, bowel impedance, and bowel pressure.

7. The medical device of claim 1, wherein the patient physiological parameter associated with the pelvic floor dysfunction is selected from the group consisting of: pudendal afferent nerve activity, sacral afferent nerve activity, and muscle activity.

8. The medical device of claim 1, wherein the patient physiological parameter associated with the pelvic floor dysfunction is motion of the patient.

9. The medical device of claim 1, wherein the ablation catheter device is configured to communicate with the processor, the processor configured to identify, based on the nerve activity measured by the sensor the distal end of the catheter body, the C fiber by distinguishing the *C fiber* from other types of nerve fibers or other non-nerve fiber tissue.

* * * * *